United States Patent
Park et al.

(10) Patent No.: US 10,600,173 B2
(45) Date of Patent: Mar. 24, 2020

(54) MULTI-OPTIC VISION DEVICE UTILIZING AREA-SCANNING FOR DETECTING DEFECTS

(71) Applicant: SAMSUNG DISPLAY CO., LTD., Yongin-si, Gyeonggi-Do (KR)

(72) Inventors: Yong-Hee Park, Yongin-si (KR); Noh Joong Park, Seoul (KR); Hyeon Suk Guak, Asan-si (KR); Ki Hun Kim, Cheonan-si (KR); Tae Yong Kim, Seoul (KR); Hye Jin Lee, Asan-si (KR); Byung Jun Jeon, Seoul (KR); Young Il Jung, Cheonan-si (KR)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 444 days.

(21) Appl. No.: 15/290,868

(22) Filed: Oct. 11, 2016

(65) Prior Publication Data
US 2017/0221193 A1     Aug. 3, 2017

(30) Foreign Application Priority Data
Aug. 12, 2015  (KR) ........................ 10-2015-0113985

(51) Int. Cl.
| | |
|---|---|
| G01N 21/958 | (2006.01) |
| G06T 7/00 | (2017.01) |
| G01N 21/88 | (2006.01) |
| G06K 9/46 | (2006.01) |
| G06T 7/60 | (2017.01) |
| H04N 5/225 | (2006.01) |

(52) U.S. Cl.
CPC ....... *G06T 7/0004* (2013.01); *G01N 21/8806* (2013.01); *G01N 21/958* (2013.01); *G06K 9/4661* (2013.01); *G06T 7/60* (2013.01); *H04N 5/2256* (2013.01); *G01N 2021/8825* (2013.01)

(58) Field of Classification Search
None
See application file for complete search history.

(56) References Cited

U.S. PATENT DOCUMENTS

| | | | |
|---|---|---|---|
| 2008/0225299 A1* | 9/2008 | Ono ....................... | G01B 11/24 356/447 |
| 2011/0026804 A1* | 2/2011 | Jahanbin ................. | G06K 9/52 382/141 |

FOREIGN PATENT DOCUMENTS

| | | | |
|---|---|---|---|
| CN | 203149688 U | * | 8/2013 |
| JP | 11-108637 | | 4/1999 |

(Continued)

*Primary Examiner* — William C Vaughn, Jr.
*Assistant Examiner* — Joseph Daniel A Towe
(74) *Attorney, Agent, or Firm* — F. Chau & Associates, LLC

(57) ABSTRACT

A multi-optic vision device includes a dark-vision lighting apparatus illuminating a defect on a subject and leaving regions that surround the defect dark. A bright-vision lighting apparatus illuminates the subject and the regions that surround the defect and leaving the defect dark. A differential-vision lighting apparatus illuminates the subject so as to stereoscopically show the defect on the subject. An area scan camera continuously imaging the subject as the dark-vision lighting apparatus, the bright-vision lighting apparatus, and the differential-vision lighting apparatus simultaneously and respectively provide light. A controller processes the image to respectively obtain a dark-vision image, a bright-vision image, and a differential-vision image of the subject.

20 Claims, 12 Drawing Sheets

(56) References Cited

FOREIGN PATENT DOCUMENTS

| | | | | |
|---|---|---|---|---|
| JP | 11108637 | A | * | 4/1999 |
| JP | 2000-162146 | | | 6/2000 |
| JP | 2009-180561 | | | 8/2009 |
| JP | 2009180561 | A | * | 8/2009 |
| KR | 10-2000-0016881 | | | 3/2000 |
| KR | 1020120129547 | | | 11/2012 |
| KR | 1020110047876 | | * | 3/2013 |

* cited by examiner

FIG. 4
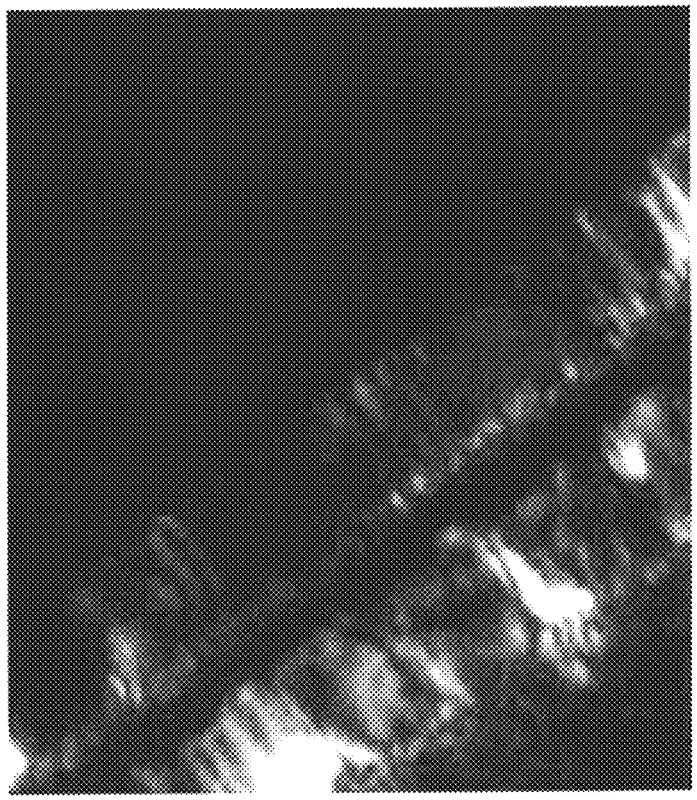
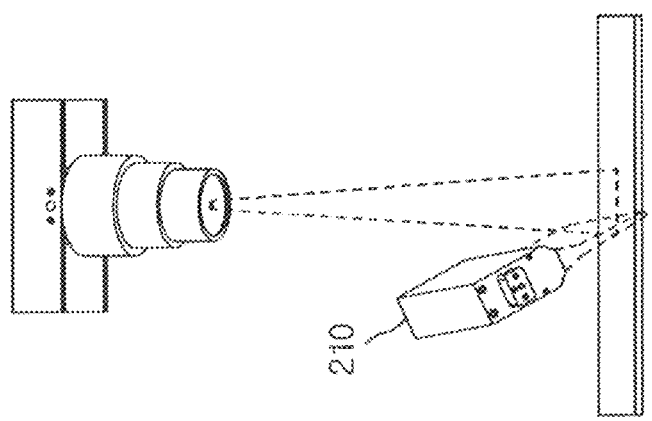

FIG. 5
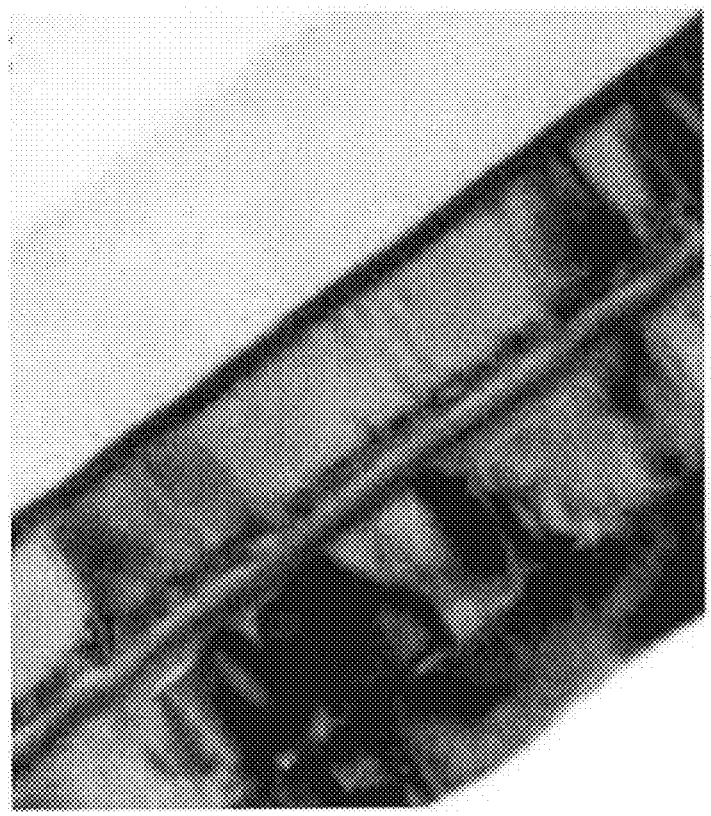
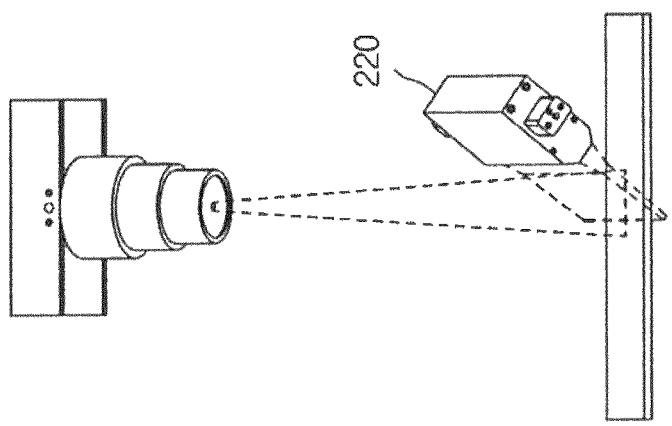

FIG. 6
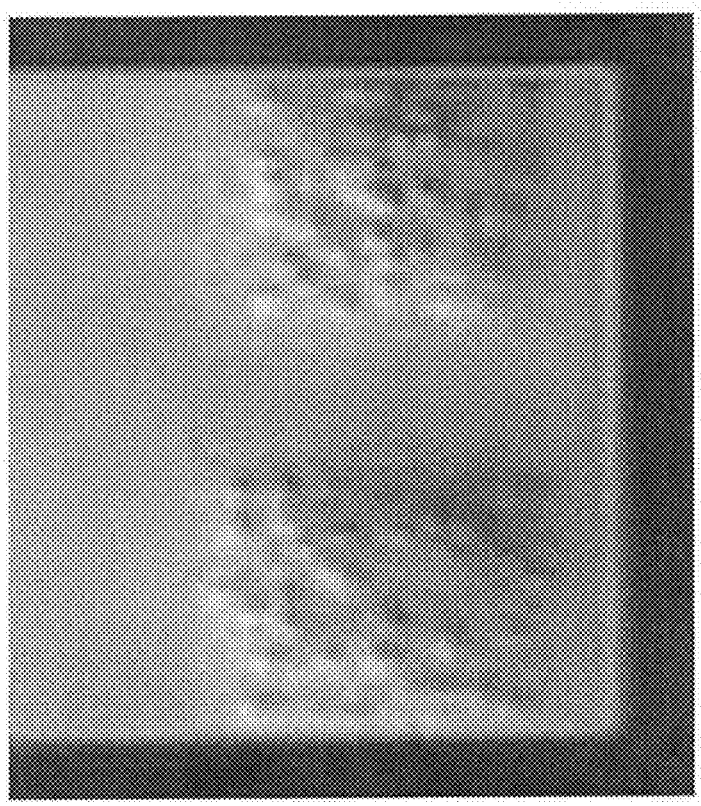
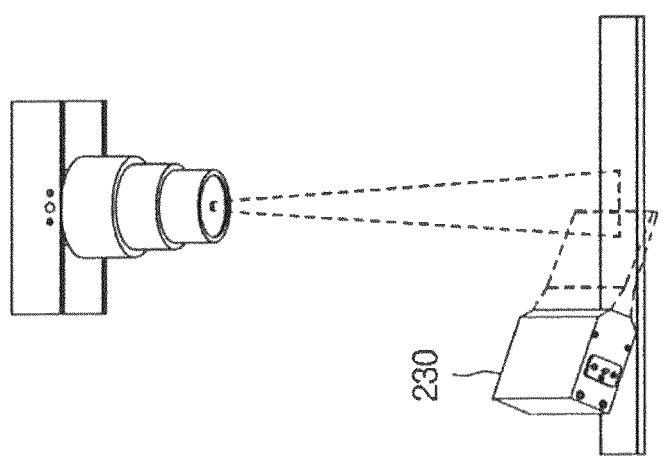

FIG. 10

| Failure name | Defect position | Detection optic | Contents |
|---|---|---|---|
| OCA | Windows / OCA Printing surface | Differential-vision | A defect generated in an OCA adhesion part of a lower end of a window (OCA wrinkling) |
| Protrusion | Windows / OCA Printing surface | Differential-vision | A defect that a window upper glass is protruded upward |
| Surface foreign | Windows / OCA Printing surface | Bright-vision | A defect that a suspended foreign is attached on a window (good product) |
| Scratch | Windows / OCA Printing surface | Dark-vision | A shape that a window surface is scratched |
| Chipping | Windows / OCA Printing surface | Bright-vision | A shape that a window outer is chipped |

MULTI-OPTIC VISION DEVICE UTILIZING AREA-SCANNING FOR DETECTING DEFECTS

CROSS REFERENCE TO RELATED APPLICATION

This application claims priority to and the benefit of Korean Patent Application No. 10-2015-0113985, filed in the Korean Intellectual Property Office on Aug. 12, 2015, the entire contents of which are herein incorporated by reference.

TECHNICAL FIELD

The present invention relates to a multi-optic vision device. More particularly, the present invention relates to a multi-optic vision device utilizing area-scanning for detecting a defect of a subject.

DISCUSSION OF THE RELATED ART

Some approaches for defect detection use a camera to capture an image of a subject. The image is then processed and analyzed to determine if a defect is present in the subject. Examples of defects that may be detected in this manner include the presence of debris or protrusions. This technology has used across many industries such as the manufacturing of flat panel displays, glass substrates, liquid crystal displays (LCDs), automotive glass, etc.

In many industries, a line scan camera is used to perform defect detection, and a lighting device is installed to illuminate the subject. However, the line scan camera may be very sensitive to the angle by which the subject is illuminated from and an angle of the line scan camera, relative to the subject. For example, if a rotation axis changes during image acquisition by even a small amount (e.g. more than 0.1 degrees), the right and left sides of the images acquired from the line scan camera may have different brightnesses. Moreover, if a vertical angle of the line scan camera is slightly changed during image acquisition, the shape of the resulting image may be distorted. Also, the lighting must be precisely controlled at a time of imaging the subject and at a time in which the subject is moved within the view of the line scan camera, as any timing problems might prevent the desired image from being properly obtained.

SUMMARY OF THE INVENTION

Exemplary embodiments of the present invention provide a multi-optic vision device for acquiring an image having a plurality of different optical characteristics without the need to control or synchronize lighting. Detection error may be reduced by using complementary image data when detecting a defect.

A multi-optic vision device includes a dark-vision lighting apparatus illuminating a defect on a subject and leaving regions that surround the defect dark. A bright-vision lighting apparatus illuminates the subject and the regions that surround the defect and leaving the defect dark. A differential-vision lighting apparatus illuminates the subject so as to stereoscopically show the defect on the subject. An area scan camera continuously imaging the subject as the dark-vision lighting apparatus, the bright-vision lighting apparatus, and the differential-vision lighting apparatus simultaneously and respectively provide light. A controller processes the image to respectively obtain a dark-vision image, a bright-vision image, and a differential-vision image of the subject.

An optical defect detection apparatus includes a movable platform with a subject disposed thereon. A first lighting apparatus illuminates the subject in a first manner. A second lighting apparatus illuminates the subject in a second manner different from the first manner. A third lighting apparatus illuminates the subject in a third manner different from the first and second manners. A camera scans an area of the subject as the subject is moved by the movable plate and outputs image data. A graphics processing device is configured to generate a first image from the image data, based on the light from the first lighting apparatus, to generate a second image from the image data, based on the light from the second lighting apparatus, and to generate a third image from the image data, based on the light from the third lighting apparatus. The second image is different from the first image, and the third image is different from the first and second image.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein:

FIG. 1 to FIG. 6 are views illustrating a multi-optic vision device according to an exemplary embodiment of the present invention;

FIG. 10 to FIG. 12 are views illustrating defects detected in a multi-optic vision device according to an exemplary embodiment of the present invention.

DETAILED DESCRIPTION OF THE EMBODIMENTS

Figure 1:
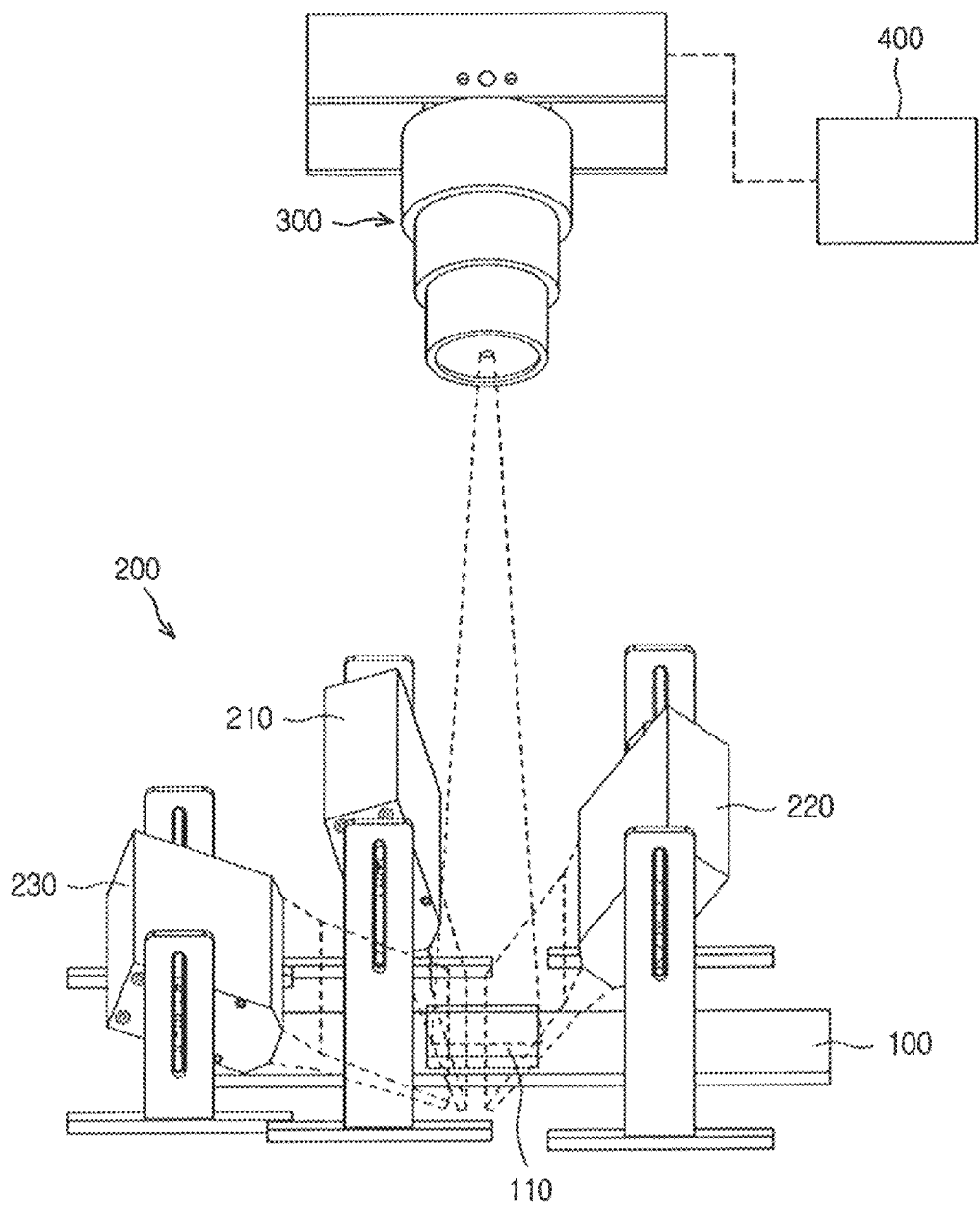

It will be apparent to those skilled in the art that various modifications and variations can be made in the present invention without departing from the spirit or scope of the invention, and specific exemplary embodiments are exemplified in the drawings and explained in the detailed description. Thus, it is intended for the present invention to cover modifications and variations of this invention provided they fall within the scope of the present invention and their equivalents. In the present specification, it is to be understood that when one component is referred to as being "connected" or "coupled" to another component, it may be connected or coupled directly to the other component or may be connected or coupled to the other component by having another component intervening therebetween.

FIG. 1 to FIG. 6 are views illustrating a multi-optic vision device according to an exemplary embodiment of the present invention.

Referring to FIG. 1, the multi-optic vision device includes a moving platform 100, a lighting apparatus 200, an area scan camera 300, and a controller 400.

The moving platform 100 moves a subject 110 for testing The moving platform 100 can move the subject 110 back and forth, left and right, or up and down. Thus the moving platform 100 may be able to position the subject 110 to any desired direction in three dimensions. The moving platform 100 may further include a fixing device to fix the subject 110 to the moving platform.

The lighting apparatus 200 illuminates the subject so that a defect of the subject 110 may be properly detected.

Figure 2:
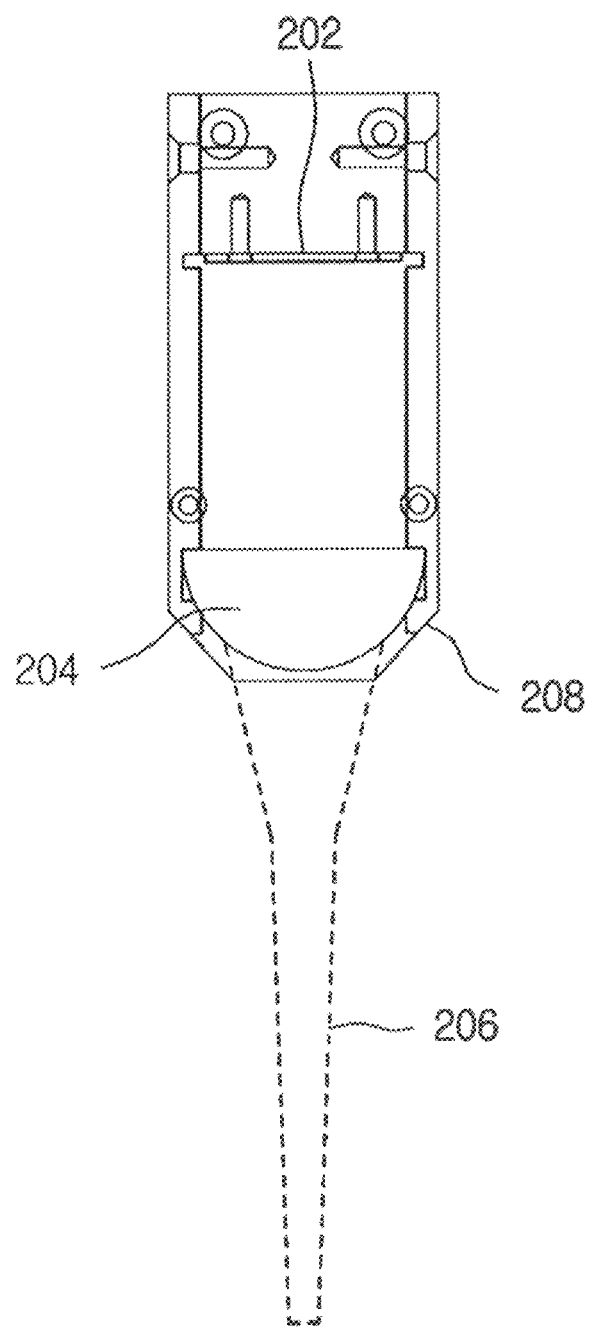

Referring to FIG. 2, the lighting apparatus 200 includes a light source unit 202, a light condensing lens 204, a light transmission unit 206, and a diffuse reflection block shielding plate 208.

The light source unit 202 generates light, and for example, may be a light emitting diode (LED). For example, the light source unit 202 may be an LED having luminous flux (Lx) of 260 Flux, a CCT range of 8300 k, and an angle of view of 125 degrees.

The light condensing lens 204 condenses the light generated from the light source unit 202 at a predetermined distance. The light condensing lens 204, for example, condenses the light at a distance of 80 mm.

The light transmission unit 206 guides the light to illuminate the subject 110 with sufficient intensity.

The diffuse reflection block shielding plate 208 encloses the lighting apparatus 200 to prevent light from escaping therefrom and to help concentrate the light. However, the diffuse reflection block shielding plate 208 has an opening and does not enclose an end of the light condensing lens 204 or the light transmission unit 206. As the light source unit illuminates various illumination regions of the subject 110, the diffuse reflection block shielding plate 208 helps to prevent interference in the light that illuminates neighboring illumination regions.

Figure 3:
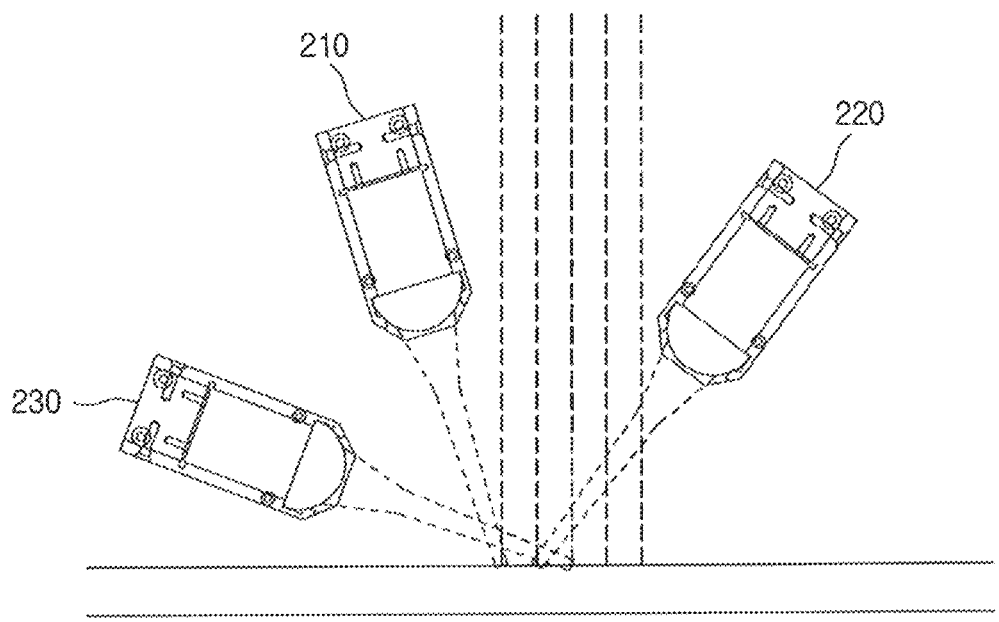

Referring to FIG. 3, the lighting apparatus 200 includes a dark-vision lighting apparatus 210, a bright-vision lighting apparatus 220, and a differential-vision lighting apparatus 230.

The dark-vision lighting apparatus 210, the bright-vision lighting apparatus 220, and the differential-vision lighting apparatus 230 differ from each other based on the angle of light emanating therefrom and the reflection angle of the light upon reflecting off of the subject 110, is the dark-vision lighting apparatus 210, the bright-vision lighting apparatus 220, and the differential-vision lighting apparatus 230 are installed to maintain a predetermined distance from the illumination region to which the light is cast. In the dark-vision lighting apparatus 210, the bright-vision lighting apparatus 220, and the differential-vision lighting apparatus 230, an illumination angle and illumination brightness may be changed depending on a physical property of the subject of the test. For the dark-vision lighting apparatus 210, the bright-vision lighting apparatus 220, and the differential-vision lighting apparatus 230, for example, in a case that a printing surface of a window glass of a smart phone is the subject, the dark-vision lighting apparatus 210 may have an illumination angle of 107 degrees based on a right plane, the bright-vision lighting apparatus 220 may have an illumination angle of 53 degrees based on the right plane, and the differential-vision lighting apparatus 230 may have an illumination angle of 165 degrees based on the right plane. For the dark-vision lighting apparatus 210, the bright-vision lighting apparatus 220, and the differential-vision lighting apparatus 230, for example, where the subject is predominantly metallic, the lighting brightness value may be decreased to ⅓ as compared with where the subject is the printing surface of the window glass of the smart phone. Moreover, the dark-vision lighting apparatus 210 may have an illumination angle of 112 degrees based on a right plane, the bright-vision lighting apparatus 220 may have an illumination angle of 48 degrees based on the right plane, and the differential-vision lighting apparatus 230 may have an illumination angle of 165 degrees based on the right plane. The dark-vision lighting apparatus 210, the bright-vision lighting apparatus 220, and the differential-vision lighting apparatus 230 may be installed such that each lighting apparatus has a desired angle of view (Field of view, FOV) of the area scan camera 300. Interference of the light at nearby illumination regions may be minimized by maintaining a predetermined distance between the installation position of the various lighting apparatuses. The multi-optic vision device, according to exemplary embodiments of the present invention, may include three lighting apparatuses to further increase the accuracy of the defect detection of the subject by obtaining the image of the plurality of optical characteristics such as the bright-vision image, the dark-vision image, and the differential-vision image, by performing only a single imaging process, without the need for lighting control or lighting synchronization.

The dark-vision lighting apparatus 210, the bright-vision lighting apparatus 220, and the differential-vision lighting apparatus 230 are described in greater detail below with reference to FIG. 4, FIG. 5, and FIG. 6, respectively.

Referring to FIG. 4, the dark-vision lighting apparatus 210 illuminates the defect to be detected. In this way, the defect may be brightly illuminated on the subject 110. The lighting angle and the lighting wavelength of the dark-vision lighting apparatus 210 may be changed depending on the physical properties of the subject, however the lighting angle of the dark-vision lighting apparatus 210 is predetermined so as to generate the diffuse reflection for the defect that may then be detected.

Referring to FIG. 5, the bright-vision lighting apparatus 220 brightly illuminates the subject including the regions that surround the defect. In this way, the defect may be left dark. The lighting angle and the lighting wavelength of the bright-vision lighting apparatus 220 may be changed depending on the physical property of the subject, however the lighting angle of the bright-vision lighting apparatus 220 is predetermined to generate a regular reflection for the defect that may then be detected.

Referring to FIG. 6, the differential-vision lighting apparatus 230 brightly illuminates the subject 110 to cast a shadow by which the defect may be detected. The light from the differential-vision lighting apparatus 230 is reflected by the surface of the subject, so that the light is scattered toward various directions. The horizontal components of the scattered light may contact with the position where the gradient of the surface of the subject is changed, therefore amount of the light that can income to the imaging apparatus such as the area scan camera 300 may be increased. Accordingly the bright image as like FIG. 6 can be obtained.

The lighting angle and the lighting wavelength of the differential-vision lighting apparatus 230 may be changed depending on the physical properties of the subject, however the lighting angle of the differential-vision lighting apparatus 230 is predetermined so that when the stereoscopic image is obtained, the angle of the shadow appears differently in each of the two views, and the defect can be identified by this difference.

The area scan camera 300 images the subject 110 while the subject 110 is simultaneously and respectively illuminated at each position by the lighting apparatus 200. The area scan camera 300 sets the imaging region of the subject in advance by the angle of view and generates an image data including the dark-vision imaging region, the bright-vision imaging region, and the differential-vision imaging region by imaging the subject at once. That is to say, the area scan camera 300 may image the subject only one-time for obtaining the image data set of the subject including the dark-vision imaging region, the bright-vision imaging region, and the differential-vision imaging region. Here, the dark-vision imaging region, the bright-vision imaging region, and the differential-vision imaging region respectively maintain the predetermined spatial interval to minimize the interference of the light that is respectively illuminated. When the subject 110 is moved by the moving platform 300, the area scan camera 300 is positioned at a vertical orientation with respect to the subject 110 to continuously image the subject 110 in the predetermined time interval, as the subject 110 is moved. Here, the predetermined time interval may be changed depending on a moving speed of the subject and a size of the imaging region of the subject. The area scan camera 300, for example, may generate the image of a pixel size 2048×2048, and according to some exemplary embodiments of the present invention, the whole subject may be imaged in a short period of time. Also, when using the instant configuration, the area scan camera 300 is not sensitive to the line lighting angle and the camera angle, as would be the case for the line scan camera described above, and, according the instant configuration, the lighting apparatus does not need a high degree of precision that depends on the imaging time of the camera and the moving time/speed of the subject. Also, since the area scan camera 300 is not sensitive to a rotation axis of the lighting apparatus, the area scan camera 300 is fixed in the vertical orientation to the plane, because the optical characteristic image is obtained in a state that the lighting apparatus is lighted, the sequential lighting control is not necessary, and a controller for additional high speed imaging and synchronized lighting control is not required.

The controller 400 processes the image to the area scan camera 300 to respectively obtain the dark-vision image, the bright-vision image, and the differential-vision image of the subject. The controller 400 separates the dark-vision imaging region, the bright-vision imaging region, and the differential-vision imaging region from each image data of the subject that is imaged at once and separately sums the separated dark-vision imaging region, bright-vision imaging region, and differential-vision imaging region, respectively, to generate the dark-vision image, the bright-vision image, and the differential-vision image of the subject.

The multi-optic vision device may further include a defect detection unit for contrasting and analyzing the generated dark-vision image, bright-vision image, and differential-vision image of the subject to detect the defect of the subject. The defect detection unit may include a microprocessor such as a graphics processing unit (GPU), or some other form of computer-processing device.

Figure 7:
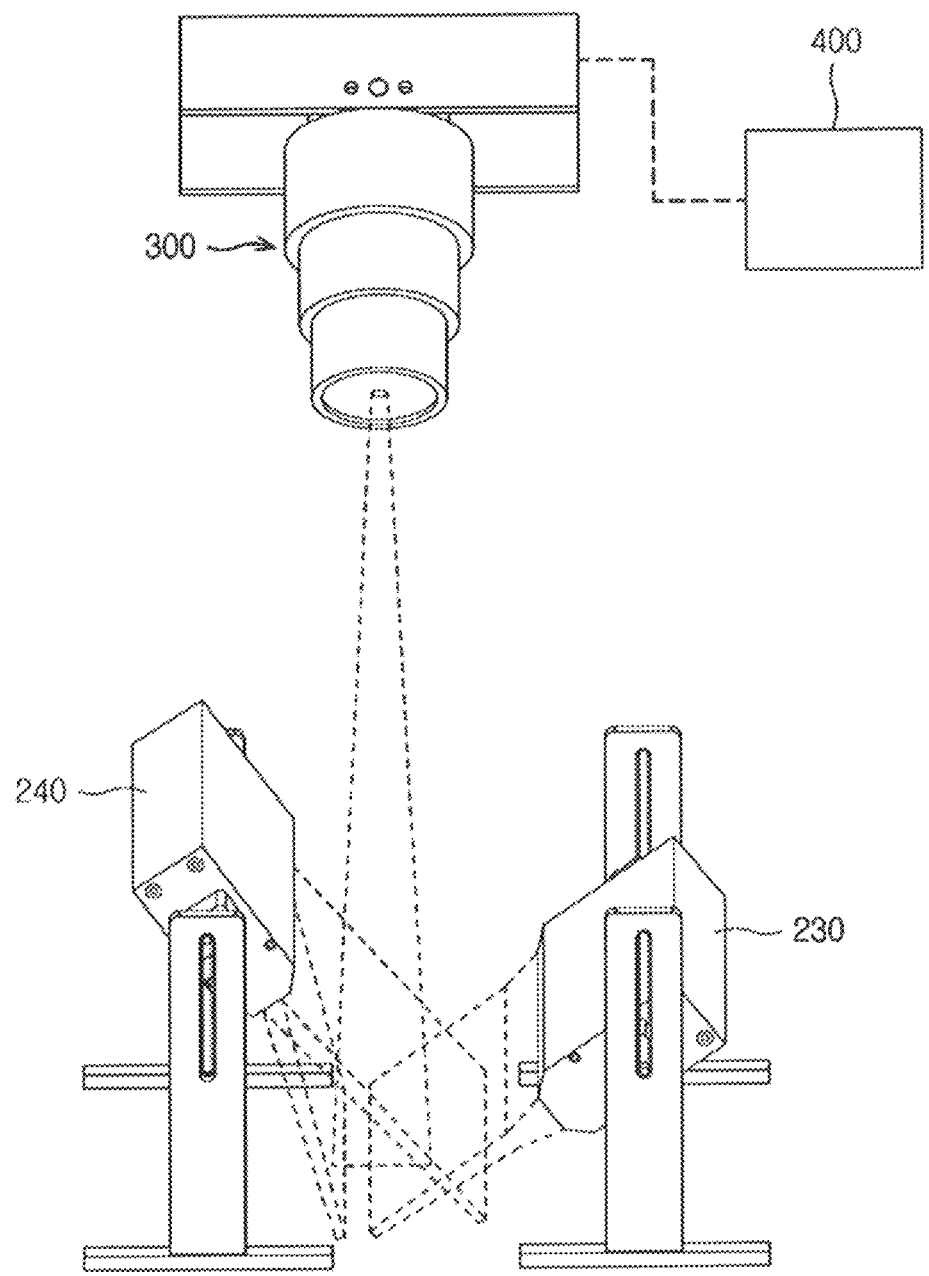
FIG. 7 and FIG. 8 are views illustrating a multi-optic vision device according to an exemplary embodiment of the present invention.
Figure 8:
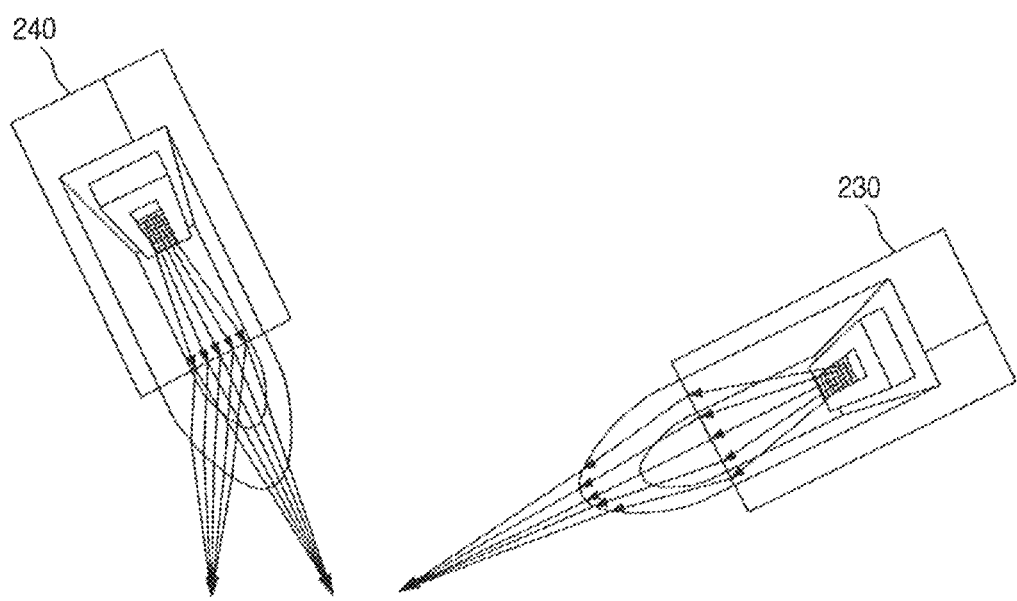

FIG. 7 and FIG. 8 are views illustrating a multi-optic vision device according to an exemplary embodiment of the present invention.

The multi-optic vision device according to an exemplary embodiment of the present invention may be the same as the multi-optic vision device described with reference to FIG. 1 to FIG. 6 except for a configuration of the lighting apparatus 200. Accordingly, only the lighting apparatus 200 will be described, and it may be assumed that all other features are similar to those described above.

Referring to FIG. 7 and FIG. 8, the multi-optic vision device according to an exemplary embodiment of the present invention includes a differential-vision lighting apparatus 230 and a bright/dark-vision lighting apparatus 240.

The differential-vision lighting apparatus 230 illuminates the subject 110 to cast a shadow of the defect. The lighting angle of the differential-vision lighting apparatus 230 is predetermined so that the shadow of the defect, as seen from two different viewing angles, may be used to identify the defect, and for example, the predetermined angle of the differential-vision lighting apparatus may be 36.3 degrees based on the right plane.

The bright/dark-vision lighting apparatus 240 simultaneously illuminates bright-vision light for the bright-vision imaging image for the subject and dark-vision light for the dark-vision imaging image for the subject while changing the illumination region of the subject. The bright/dark-vision lighting apparatus 240 uses the diffuse reflection of the light condensing lens 204 and casts the light along two distinct paths including a path in which the light is refracted and condensed in the lens and a path in which the light is diffused. The bright/dark-vision lighting apparatus 240 may differentiate the configuration of the light transmission unit 206 and the diffuse reflection block shielding plate 208 to obtain the diffuse reflection path.

The multi-optic vision device according to an exemplary embodiment of the present invention reduces the number of lighting apparatus used through the bright/dark-vision lighting apparatus 240, thereby reducing the amount of test equipment and a cost thereof.

Figure 9:
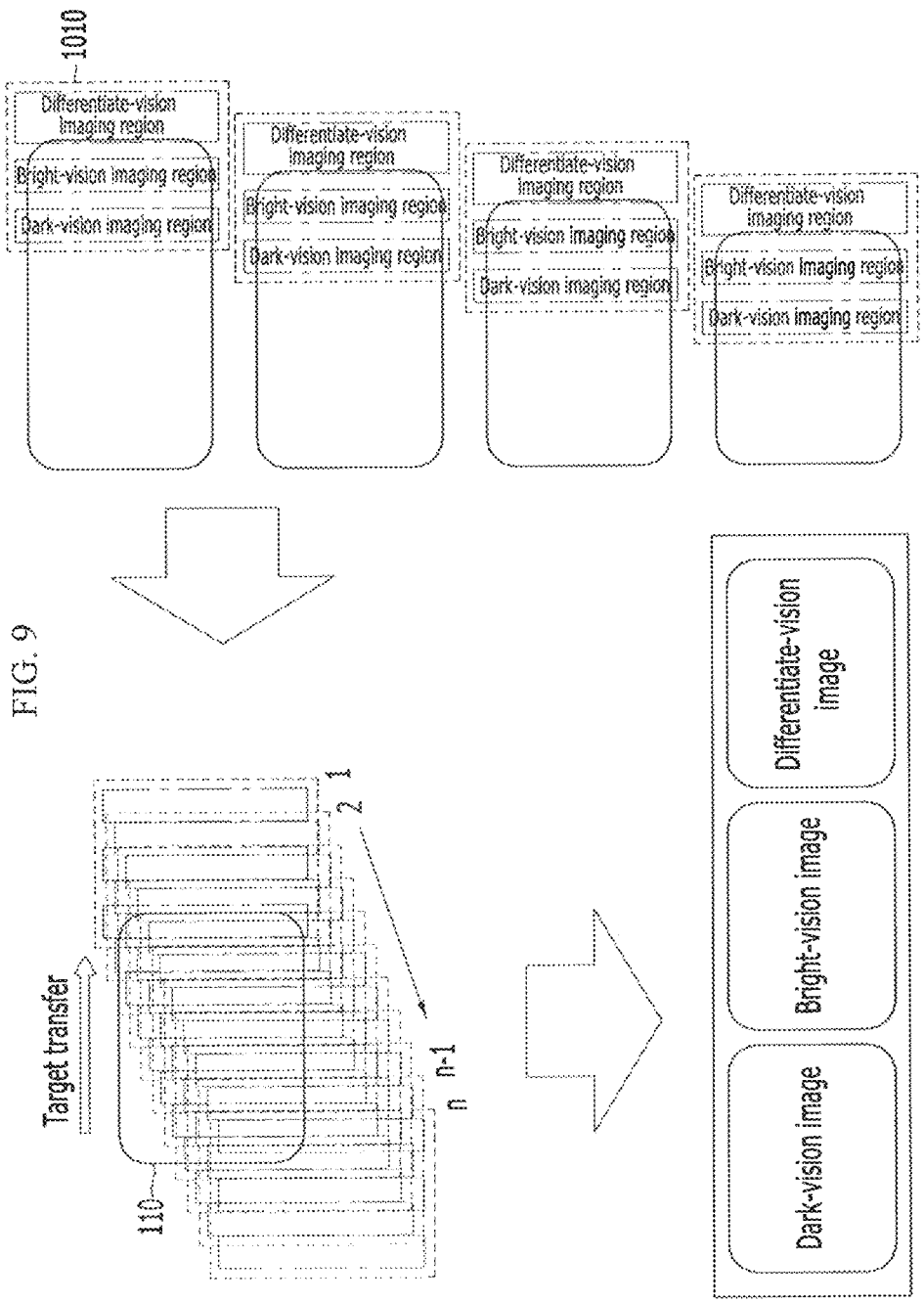
FIG. 9 is a view illustrating a method for acquiring an image using a multi-optic vision device according to an exemplary embodiment of the present invention.

FIG. 9 is a view illustrating an image obtaining method of a multi-optic vision device according to an exemplary embodiment of the present invention.

Referring to FIG. 9, as the test subject moves, the multi-optic vision device continuously images the subject 110 that is illuminated with the light from the dark-vision lighting apparatus 210, the bright-vision lighting apparatus 220, and the differential-vision lighting apparatus 230. Also, according to an exemplary embodiment of the present invention, the multi-optic vision device may continuously image the subject 110 that is illuminated with the light from the differential-vision lighting apparatus 230 and the bright/dark-vision lighting apparatus 240. The multi-optic vision device generates the image including the dark-vision imaging region, the bright-vision imaging region, and the differential-vision imaging region. Here, the size of the image and the imaging region may be set in advance according to the angle of view of the area scan camera 300. The multi-optic vision device stores the N (where N is a positive integer) imaged images. Here, N is changes depending on the imaging region and N is predetermined according to the angle of view of the area scan camera 300, and may be a value calculated by dividing the area of all regions of the subject by the area of the dark-vision imaging region, the area of the bright-vision imaging region, or the area of the differential-vision imaging region. The multi-optic vision device separates the dark-vision imaging region, the bright-vision imaging region, and the differential-vision imaging region from the N images that are sequentially imaged and stored, and separately sums the separated dark-vision imaging region, bright-vision imaging region, and differential-vision imaging region, respectively, to generate the dark-vision image, the bright-vision image, and the differential-vision image of the subject.

Figure 11:
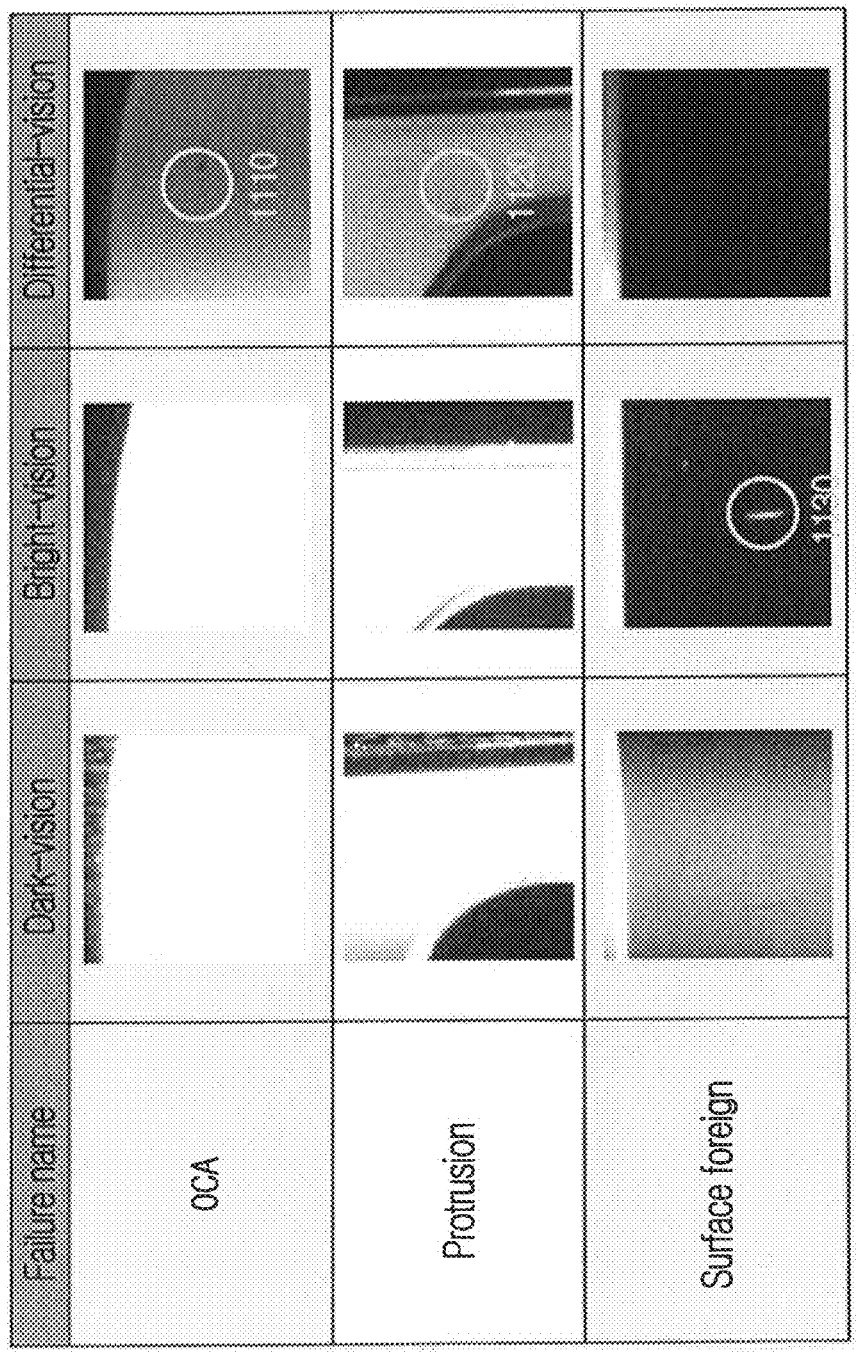
Figure 12:
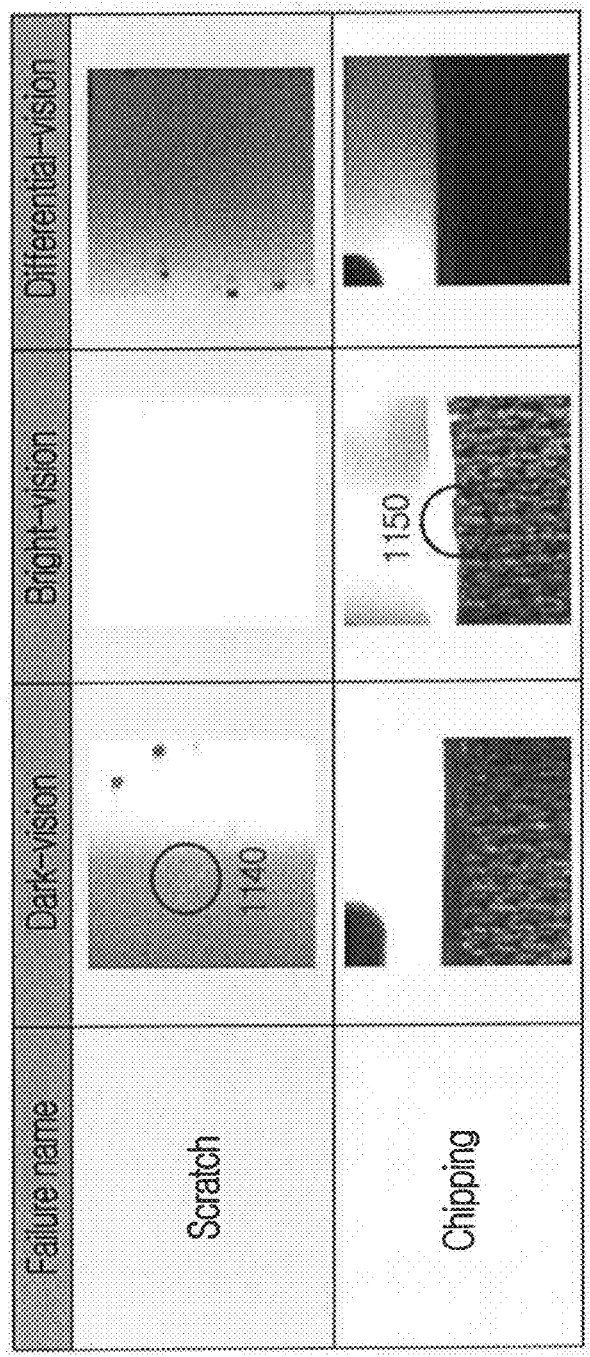

FIG. 10 to FIG. 12 are views illustrating defects detected in a multi-optic vision device according to an exemplary embodiment of the present invention.

Referring to FIG. 10 to FIG. 12, the multi-optic vision device may be configured to detect various types of defects of the subject 110. The multi-optic vision device, for example, may detect an optically clear adhesive (OCA)

defect, a protrusion defect, a surface foreign matter defect, a scratch defect, and a chipping defect that may be generated in the display device.

The optically clear adhesive (OCA) defect 1110 may be a defect generated as the OCA adhered to a lower end of the window is wrinkled. This form of defect may be detected through the differential-vision data.

The protrusion defect 1120 may be a defect in which a window upper glass is slightly protruded. This form of defect may also be detected through the differential-vision data.

The surface foreign matter defect 1130 may be a defect of which a suspended foreign material is attached on the window. This form of defect may be detected through the bright-vision image.

The scratch defect 1140 may be a defect in which the window surface is scratched. This form of defect may be detected through the dark-vision image.

The chipping defect 1150 may be a defect in which an outer part of the window is broken. This form of defect may be detected through the bright-vision image.

The multi-optic vision device according to exemplary embodiments of the present invention generates the dark-vision image, the bright-vision image, and the differential-vision image at the same time through the area scan camera 300, and may quickly and correctly detect each of the above-described defects by comparing the dark-vision image, the bright-vision image, and the differential-vision image. For example, the defect of the subject may be classified into an invisible defect and a visible defect depending an optical setting. Exemplary embodiments of the present invention may simultaneously identify these defects by comparing the dark-vision image, the bright-vision image, and the differential-vision image. For example, in the bright-vision optical setting, suspended foreign material, that is not an actual defect, is darkly expressed and an inner actual foreign material, that is an actual defect, is brightly expressed. The presence of the suspended foreign material may be removed from the image by applying the black region data in the bright-vision image to the position of the other dark-vision image and differential-vision image. By removing the presence of the inner foreign material, but not the suspended foreign material, false positive defect detection may be reduced or eliminated.

The image obtaining methods described herein of the multi-optic vision device according to exemplary embodiments of the present invention may be realized as a program instruction format executable through a processing device for processing various electronic information and may be recorded on a storage medium. The storage medium may include program instructions, file data, and data structures, or combinations thereof. The program instructions recorded on the storage medium may be those that are designed and configured for the present invention, or those that are known to a person of ordinary skill in the art of computer software and are usable. Examples of the storage medium include magnetic media such as a hard disk drive, a floppy disk, or a magnetic tape, optical media such as a CD-ROM, a DVD, or a BLU-RAY DISC, magneto-optical media such as a floptical disk, and a hardware device specially configured to store and execute program instructions such as a ROM, a RAM, or a flash memory. Examples of the program instructions include high-level language codes executable by a device electronically processing information, for example, a computer, by using an interpreter in addition to machine language codes generated by a compiler. The hardware device can be configured to be operable as at least one software module fir performing an operation of the present invention.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the present disclosure.

What is claimed is:

1. A multi-optic vision device, comprising:

a dark-vision lighting apparatus illuminating a defect on a subject and leaving regions that surround the defect dark;

a bright-vision lighting apparatus illuminating the subject including the regions that surround the defect and leaving the defect dark;

a differential-vision lighting apparatus illuminating the subject so as to stereoscopically show the defect on the subject;

a single area scan camera imaging the subject as the dark-vision lighting apparatus, the bright-vision lighting apparatus, and the differential-vision lighting apparatus simultaneously and respectively provide light so as to generate image data in which a dark-vision image, a bright-vision image, and a differential-vision image are all combined, by performing a single imaging process; and a controller processing the image to respectively obtain the dark-vision image, the bright-vision image, and the differential-vision image of the subject from the combined image and separates a dark-vision imaging region, a bright-vision imaging region, and a differential-vision imaging region from each image data of the subject and separately sums the separated dark vision imaging region, the bright-vision imaging region, and the differential-vision imaging region, respectively, to generate the dark-vision imagine, the bright-vision image, and the differential-vision image of the subject.

2. The multi-optic vision device of claim 1, wherein the dark-vision lighting apparatus, the bright-vision lighting apparatus, and the differential-vision lighting apparatus are spaced apart from one another by a distance that is determined according to an angle at which the light is cast upon the subject by the dark-vision lighting apparatus, the bright-vision lighting apparatus, and the differential-vision lighting apparatus.

3. The multi-optic vision device of claim 2, wherein the dark-vision lighting apparatus, the bright-vision lighting apparatus, and the differential-vision lighting apparatus each create at least one illumination region where the subject is illuminated by each light.

4. The multi-optic vision device of claim 1, wherein the dark-vision lighting apparatus, the bright-vision lighting apparatus, and the differential-vision lighting apparatus each cast light at a different angle and each provide a brightness of the light that depends on a physical property of the subject.

5. The multi-optic vision device of claim 1, wherein at least one of the dark-vision lighting apparatus, the bright-vision lighting apparatus, and the differential-vision lighting apparatus includes:
  a light source unit generating the light; a light condensing lens condensing the generated light;
  a light transmission unit concentrating and casting the condensed light; and
  a diffuse reflection block shielding plate.

6. The multi-optic vision device of claim 1, wherein the area scan camera generates N images including at the dark-vision imaging region, the bright-vision imaging region, and the differential-vision imaging region having a predetermined interval, wherein N is a positive integer.

7. The multi-optic vision device of claim 6, further comprising a moving platform moving the subject, wherein N is changed depending on an imaging region that is predetermined by a moving speed of the subject that is moved by the moving platform and the angle of view of the area scan camera.

8. The multi-optic vision device of claim 6, wherein the controller respectively separates the dark-vision, imaging region, the bright-vision imaging region, and the differential-vision imaging region from the N imaging images and respectively sums the separated dark-vision imaging region, the bright-vision imaging region, and the differential-vision imaging region to generate the dark-vision image, the bright-vision image, and the differential-vision image.

9. The multi-optic vision device of claim 1, wherein the dark-vision lighting apparatus and the bright-vision lighting apparatus are integrated into one lighting apparatus such that the illumination region is differentiated through a refraction of different angles and the subject is simultaneously illuminated.

10. The multi-optic vision device of claim 1, further comprising a defect detection unit processing the dark-vision image, the bright-vision image, and the differential-vision image of the subject to detect the defect of the subject.

11. An optical defect detection apparatus, comprising:
  a movable platform with a subject disposed thereon;
  a first lighting apparatus illuminating the subject in a first manner;
  a second lighting apparatus illuminating the subject in a second manner different from the first manner;
  a third lighting apparatus illuminating the subject in a third manner different from the first and second manners;
  a single camera that scans an area of the subject as the subject is moved by the movable plate and outputs image data representing light reflected from the subject that is simultaneously provided by the first lighting apparatus, the second lighting apparatus, and the third lighting apparatus so as to generate image data in which a first-light image, a second-light image, and a third-light image are all combined, by performing a single imaging process; and
  a graphics processing device configured to obtain the combined image data so as to generate a first image from the image data, based on the light from the first lighting apparatus, to generate a second image from the image data, based on the light from the second lighting apparatus, and to generate a third image from the image data, based on the light from the third lighting apparatus,
  wherein the second image is different from the first image, and the third image is different from the first and second image, and
  wherein the graphics processing device separates a first imaging region, a second imaging region, and a third imaging region from each image data of the subject and separately sums the separated the first imaging, the second imaging region, and the third imaging region, respectively, to generate the first image, the second image, and the third image of the subject.

12. The optical defect detection apparatus of claim 11, wherein the graphics processing device is further configured to detect a first type of defect from the first image and to detect a second type of defect from the second or third images.

13. The optical defect detection apparatus of claim 11, wherein the graphics processing device is further configured to detect a defect by comparing the first image to either the second or third image.

14. The optical defect detection apparatus of claim 11, wherein the graphics processing device is further configured to produce a stereoscopic image from the third image.

15. The optical defect detection apparatus of claim 11, wherein the first lighting apparatus includes a dark-vision lighting apparatus, the second lighting apparatus includes a bright-vision lighting apparatus, and the third lighting apparatus includes a differential-vision lighting apparatus.

16. The optical defect detection apparatus of claim 15, wherein the dark-vision lighting apparatus illuminates the defect on the subject and leaves regions that surround the defect dark, the bright-vision lighting apparatus illuminates the subject and the regions that surround the defect and leaving the defect dark, and the differential-vision lighting apparatus illuminates the subject so as to stereoscopically show the defect on the subject.

17. The optical defect detection apparatus of claim 11, wherein at least one of the first, second, or third lighting apparatus includes:
  light source unit generating the light;
  a light condensing lens condensing the generated light;
  a light transmission unit concentrating and casting the condensed light; and
  a diffuse reflection block shielding plate.

18. The optical defect detection apparatus of claim 17, wherein the diffuse reflection block shielding plate encloses the light source unit to prevent light from escaping therefrom and has an opening that leaves the light transmission unit unenclosed.

19. The optical defect detection apparatus of claim 11, wherein the first, second and third lighting apparatuses are fixed so as to maintain a constant angle with respect to a plane of the movable platform and to maintain a fixed separation distance with respect to each other.

20. The optical defect detection apparatus of claim 11, wherein the camera is an area scan camera.

* * * * *